United States Patent [19]
Bornstein et al.

[11] Patent Number: 5,436,454
[45] Date of Patent: Jul. 25, 1995

[54] OPTICAL PROBE FOR REMOTE ATTENUATED TOTAL REFLECTANCE MEASUREMENTS

[75] Inventors: Aharon Bornstein, Rishon Lezion, Israel; Stephen R. Lowry, Madison, Wis.

[73] Assignee: Nicolet Instrument Corporation, Madison, Wis.

[21] Appl. No.: 138,631

[22] Filed: Oct. 15, 1993

[51] Int. Cl.⁶ .................... G01N 21/01; G01N 21/31; G01N 21/35
[52] U.S. Cl. .................... 250/339.12; 250/339.07; 250/339.11; 250/341.2; 250/341.8; 356/300
[58] Field of Search ............. 250/341, 339.07, 339.08, 250/339.12, 341.1, 341.2, 341.8, 339.11, 340; 356/133, 300, 436

[56] References Cited

U.S. PATENT DOCUMENTS

| | | |
|---|---|---|
| Re. 33,789 | 1/1992 | Stevenson . |
| 3,433,570 | 3/1969 | Hansen ................. 356/128 |
| 3,470,261 | 9/1969 | Roberts ................. 585/401 |
| 3,669,545 | 6/1972 | Gilby ................... 356/320 |
| 4,427,293 | 1/1984 | Harmer ................. 356/133 |
| 4,540,280 | 9/1985 | Anderson et al. . |
| 4,799,001 | 1/1989 | Burch . |
| 4,829,186 | 5/1989 | McLachlan et al. ........ 250/373 |
| 4,847,878 | 7/1989 | Badeau . |
| 5,070,243 | 12/1991 | Bornstein et al. . |
| 5,097,129 | 3/1992 | de Vries et al. .......... 250/341 X |
| 5,153,675 | 10/1992 | Beauchaine . |
| 5,185,834 | 2/1993 | Day et al. . |
| 5,218,656 | 6/1993 | Day et al. . |
| 5,239,176 | 10/1993 | Stevenson . |

FOREIGN PATENT DOCUMENTS

| | | |
|---|---|---|
| 57667 | 8/1982 | European Pat. Off. ....... 356/133 |
| 507752 | 10/1992 | European Pat. Off. ....... 250/341 |
| 57-111423 | 7/1982 | Japan ................... 250/341 |
| 2-236145 | 9/1990 | Japan ................... 356/133 |

OTHER PUBLICATIONS

N. J. Harrick, *Internal Reflection Spectroscopy* (book), Harrick Scientific Corporation, New York, N.Y., 1979, pp. 40–41, 89–97.

David A. Krohn, *Fiber Optic Sensors Fundamentals and Applications* (book), Instrument Society of America, Research Triangle Park, N.C., 1988, pp. 12–13.

P. Poscia, et al., "Biochemical Measurement of Bilirubin With an Evanescent Wave Optical Sensor," SPIE, vol. 1510, Chemical and Medical Sensors, 1991, pp. 112–117.

*Primary Examiner*—Constantine Hannaher
*Assistant Examiner*—Edward J. Glick
*Attorney, Agent, or Firm*—Foley & Lardner

[57] ABSTRACT

A probe for use in attenuated total reflectance measurements in spectroscopy, such as Fourier transform infrared spectroscopy, is formed of an optical waveguide element having input and output sections and a loop between the two sections. The loop has a small radius of curvature and is exposed so that it can be contacted with a sample to obtain attenuated total reflectance measurements. The input and output sections may be retained in the bore of a thin walled tube with the loop forming a tip which extends from one end of the tube. The input and output sections of the optical waveguide element may be connected by couplers to a spectrometer to receive the output beam from and provide a return beam to the spectrometer. The tightly curved surfaces of the optical waveguide element at the loop result in multiple internal reflections as the beam of radiation traverses the loop. Attenuated total reflectance interactions occur between the beam of radiation and sample material in contact with the loop, which can comprise a liquid, a gas, or relatively soft solid materials.

29 Claims, 6 Drawing Sheets

OPTICAL PROBE FOR REMOTE ATTENUATED TOTAL REFLECTANCE MEASUREMENTS

FIELD OF THE INVENTION

This invention pertains generally to the field of spectroscopy, and more particularly to spectroscopy utilizing attenuated total reflectance techniques.

BACKGROUND OF THE INVENTION

A variety of spectroscopic equipment has been developed for analyzing the absorption and transmission of electromagnetic radiation by a sample at various wavelengths to determine chemical characteristics of the sample. One type of spectroscopic instrument now widely used is a Fourier transform infrared (FTIR) spectrometer. FTIR spectrometers typically incorporate a Michelson interferometer having a moving mirror. The interferometer modulates the infrared beam from an infrared source to produce an output beam in which the intensity of the infrared radiation at various wavelengths is periodically varied. The output beam is typically focused and passed through, or reflected from, a sample, after which the beam is collected and focused onto a detector. The detector provides a time varying output signal which contains information concerning the wavelengths of infrared absorbance, or specular reflectance, of the sample. Fourier analysis is performed on the output signal data to yield usable information on the chemical composition of the sample.

It is often desirable to do spectroscopic analyses on gases and liquids, including flowing gases and liquids, and, in some cases, on solids. In many of these situations, it is not convenient or desirable to remove a sample of the material and place it in the sample chamber of the spectrometer for analysis.

One approach to interfacing the beam of analytical radiation from the spectrometer with a liquid or gas sample is the use of an attenuated total reflectance (ATR) probe. In ATR devices, the optical element is shaped so that radiation enters through one face of the element, passes along the element, and exits through another face. Between the entrance and exit, the radiation makes a number of total internal reflections from the sidewalls of the element. The sidewalls of the element are in contact with a liquid or gas sample, and as a consequence of the physical phenomenon of internal reflectance, the analytical radiation is selectively attenuated at certain wavelengths characteristic of the sample material in contact with the exposed face of the ATR optical element. A variety of designs for optical elements for ATR probes are described in the book by N. J. Harrick, *Internal Reflection Spectroscopy*, Harrick Scientific Corporation, New York, 1979.

The optical elements for ATR probes are commonly crystals having highly polished flat surfaces which interface with the sample. One type of prior probe uses a cylindrical ATR crystal having a conical end which acts as the interface with the sample. Such optical elements must be precisely polished and thus are generally expensive to produce and expensive to replace if the polished surfaces become scratched or damaged. Where ATR cells are used at a location remote from the spectrometer, optical fiber cables are sometimes used to transmit the incoming beam to the ATR probe and to return the beam from the probe to the spectrometer. Focusing optics are generally required to receive the radiation from the end of the first fiber optic cable and direct it through the input face of the ATR optical element. The analytical radiation passed from the output face of the ATR optical element must then be collected and focused onto the end of the optical fiber cable connected to the spectrometer. The need for such focusing optics makes assembly of such ATR probes more difficult and expensive. Typically, ATR probes are also relatively large because of the need for focusing optics and the relatively large ATR optical element. These probes are also difficult to use with commercial tube fittings commonly found in process lines and chemical reactors, and typically require at least ¼ inch diameter fittings.

SUMMARY OF THE INVENTION

In accordance with the present invention, an optical probe for attenuated total reflectance measurements is formed of an optical waveguide element having a loop therein which is available to contact a sample to allow a beam of analytical radiation (e.g., infrared) passed through the optical waveguide to interact with the sample. The tightly curved surfaces of the optical waveguide element at the loop result in multiple internal reflections as the beam of radiation traverses the loop. These multiple reflections are much more frequent than would occur in a straight section of a similar length of optical waveguide. Consequently, a significant interaction between the sample and the analytical radiation exhibiting the attenuated total reflectance effect will occur at the loop, allowing the radiation returned from the optical waveguide to be analyzed in a spectrometer to determine the chemical composition of the sample.

The probe may be formed of an optical waveguide element having an input section, an output section, and a loop between the input and output sections, all preferably formed integrally. The input and output sections preferably extend away from the loop adjacent to one another, with the waveguide element traversing, in effect, 180 degrees through the loop. A preferred probe structure includes an elongated hollow tube or cannula having a bore through which the input and output optical waveguide sections extend, with the loop protruding from one end of the tube. The loop may be secured to the tube with an appropriate sealing material, such as epoxy, which also seals the end of the tube but leaves the loop exposed. The ends of the input and output sections may have conventional fiber optic couplers attached thereto to allow fiber optic cables to be connected to the probe to transmit the radiation to and from the spectrometer. Focusing optics are generally not needed at these couplers. Alternatively, the input and output sections of the probe may themselves be long enough and sufficiently shielded to provide integral optical cables which can extend back to a spectrometer located at a remote position from the probe.

The loop which forms the tip of the probe may be formed relatively small and sharp, allowing the probe to be used to probe the chemical composition of relatively small amounts of material, including spots of relatively soft solid material which can be contacted by the loop forming the probe tip. A sufficiently thin cannula having the probe tip mounted thereon may be utilized for in vivo measurements, as by inserting the probe under the skin or into a blood vessel of a living subject. The probe of the present invention is also well adapted to be inserted into process and fluid lines to sample the fluid flowing in the lines. For example, a standard connector fitting may be used to allow the probe to be inserted into a flow line and sealed thereto and to obtain measurements on the fluid flowing in the line.

The optical waveguide forming the input and output sections and the loop tip may be made from a variety of materials, the choice of which depends in part on the wavelength of the analytical radiation being utilized. For infrared radiation, a chalcogenide glass has been found suitable and is readily formable by heating. The dimensions of the optical waveguide element may be chosen as desired, with typical diameters in the range of 0.1 to 1 millimeter (mm), and with a radius of curvature of the loop preferably being as small as possible, typically slightly more than the diameter of the waveguide itself. The minimum radius of curvature is selected so that the radiation generally will be internally reflected rather than striking the walls of the optical waveguide in the turn at such high angles as to escape the optical waveguide.

The probe of the present invention thus can be formed to have lower cost and smaller overall size and diameter than conventional ATR probes, and with the input and output beam connections extending in the same direction, thereby minimizing the space required for such connections.

Further, objects, features and advantages will be apparent from the following detailed description when taken in conjunction with the accompanying drawings.

DETAILED DESCRIPTION OF THE INVENTION

Figure 1:
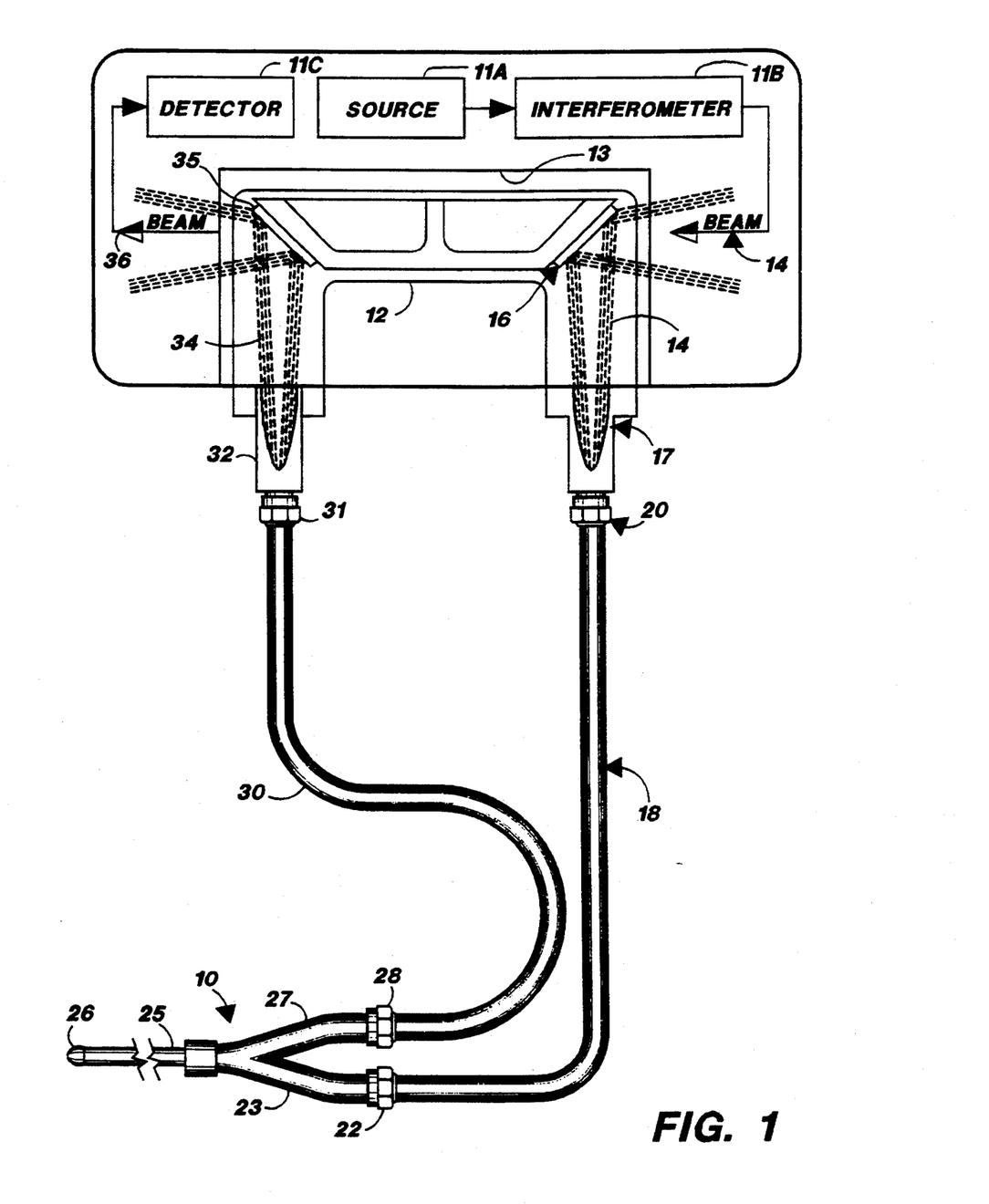
FIG. 1 is an illustrative view of a spectroscopic system utilizing an optical probe in accordance with the present invention located at a position remote from a spectrometer.

With reference to the drawings, an optical probe for attenuated total reflectance (ATR) measurements is shown generally at 10 in FIG. 1 connected in a spectroscopy system which includes a spectrometer 11 and an optical cable interface unit 12 mounted in the sample chamber 13 of the spectrometer. The spectrometer 11 may be any of various types of spectrometers which provide a beam of analytical electromagnetic radiation which is affected by the sample and then analyzed. For example, the spectrometer 11 may be a commercially available Fourier transform infrared (FTIR) spectrometer such as a Nicolet Magna 750 spectrometer from Nicolet Instrument Corporation. As is conventional in FTIR spectrometers, the spectrometer 11 includes an infrared source 11A, an interferometer 11B receiving the beam from the source and providing a modulated output beam 14, a detector 11C, and various conventional optical elements (not shown). Examples of FTIR spectrometer optical systems are shown in U.S. Pat. Nos. 4,799,001, 4,847,878, and 5,153,675, which are incorporated herein by reference. The output beam 14 from the spectrometer is provided to the interface unit 12 where it is reflected off a mirror 16 and concentrated on a coupling unit 17 of standard design which is connected to a fiber optic cable 18 by a connection 20. The fiber optic cable 18 is of standard construction and allows for passage of the radiation (e.g., infrared) without substantial attenuation to locations which may be quite remote from the spectrometer 11, typically several feet away. The fiber optic cable 18 is connected by standard connector 22 to the input side 23 of the probe 10. The probe 10 has an elongated tube section 25 and a sensor tip 26, both described more fully below. When the tip 26 is in contact with a sample, e.g., a liquid, gas or a soft solid material, the beam received from the cable 18 will interact through the attenuated total reflectance effect at the tip 26, and the radiation from the tip will be passed through an output section 27 of the probe 10 and through a coupler 28 to a return fiber optic cable 30. The fiber optic cable 30 is connected by a standard connector, e.g., a connector 31, to a coupler 32 of the interface unit 12. The radiation emitted from the end of fiber optic cable 30 spreads as a beam 34 which is reflected by a mirror 35 back to the spectrometer 11 for detection by the detector 11C and analysis.

As noted, because the cables 18 and 30 will transmit analytical radiation to and from the probe 10 with very little attenuation, the probe 10 may be located at a significant distance from the spectrometer, typically several feet. Thus, the probe 10 may be located in a location where the spectrometer would not be conveniently or safely mounted, and may be used to sample materials in very small spaces, and to contact very small areas of a sample. Moreover, the probe 10 is relatively moveable, so that an operator can simply carry the probe from one location to another to sample different items with relatively little effort. For example, the probe may be utilized by inserting the probe in a liquid sample held in a first container, obtaining a spectrum from the spectrometer, and then removing the probe, cleaning it, and then dipping it into another liquid sample and obtaining a spectrum. This process may be repeated several times at a relatively rapid pace. Consequently, spectroscopic information may be obtained on a number of test samples much more rapidly than would be the case, if for example, the samples had to be mounted in a sample holder and inserted in the sample compartment of the spectrometer. In addition, the relatively small size of the probe tip 26 allows it to be pressed against solid materials, such as plastics, skin, gels, and so forth which will yield somewhat to the pressure of the probe, thereby allowing remote testing of solid specimens without having to remove a portion of the specimen to mount it in a sample chamber for analysis.

Figure 2:
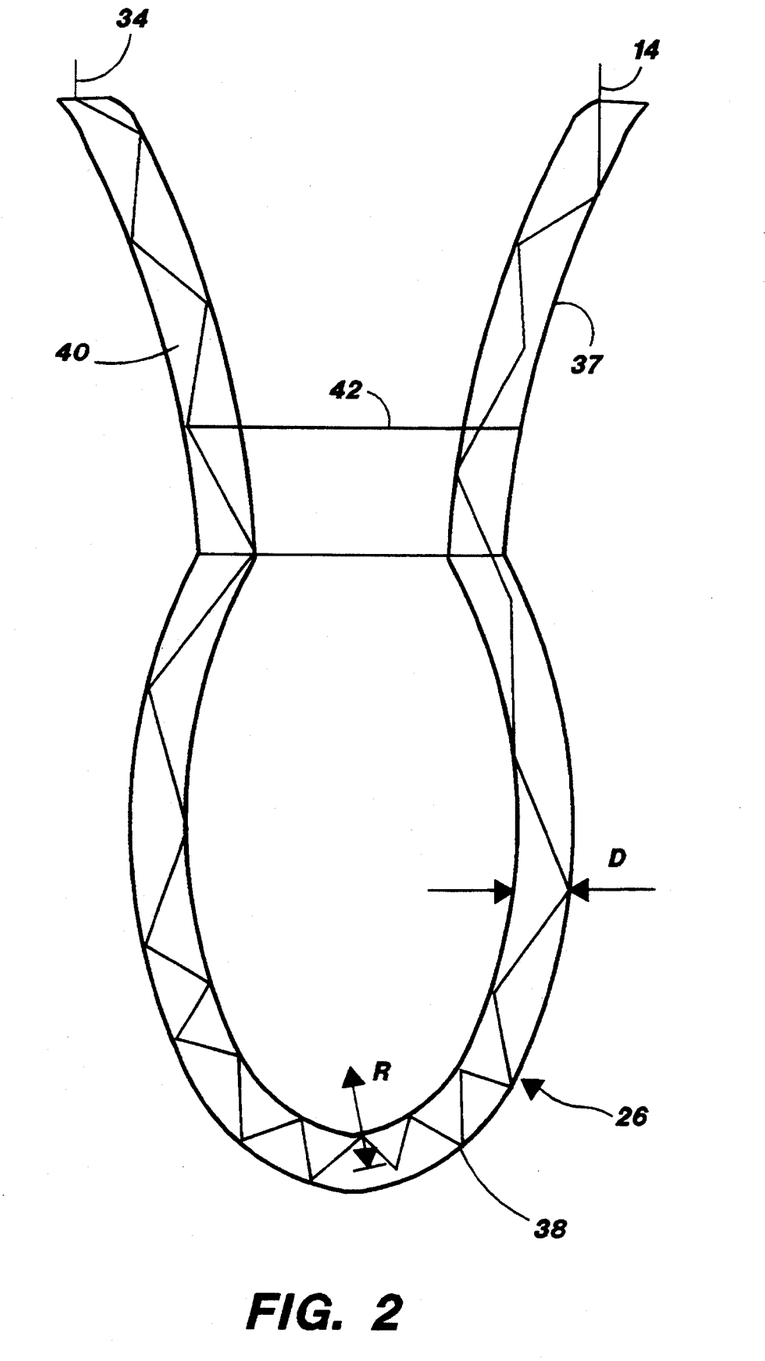
FIG. 2 is an illustrative schematic view showing the manner in which an optical beam will undergo multiple reflections in the loop forming the sensing tip of the optical probe of the invention.

A schematic view of the tip 26, and adjacent portions of the optical waveguide element, illustrating the principles of the present invention, is shown in FIG. 2. The input beam of radiation 14 enters an input section 37 of an optical waveguide element, typically making reflections off the walls of the input section 37 in the manner shown. The beam of radiation then enters the loop section 38 at the tip 26 of the optical waveguide element, which preferably is integrally formed with the input section 37. The loop 38 is an optical waveguide element which has a fairly sharp curve with its smallest radius of curvature R at the tip. After the beam passes through the loop 38, it enters an output section 40 of optical waveguide element, and exits the output section 40 as the output beam 34. In the output section 40 the beam makes multiple reflections off the walls of the output section waveguide at a frequency similar to the frequency of reflection from the walls of the input section 37. However, in the loop 38, the curvature of the loop causes the beam of radiation to strike the walls more frequently per unit length, and at a sharper angle, as illustratively shown in FIG. 2. Sample material in the region surrounding the loop 38 and in contact with the optical material of the optical waveguide forming the loop 38 will interact with the radiation beam within the loop to provide the attenuated total reflectance effect.

Generally, it is preferred that the radius R of the sharpest portion of the loop 38 be selected relative to the diameter D of the waveguide element so as to maximize the number of internal reflections through the loop 38, while not increasing the angle of reflection to the point where a substantial portion of the beam strikes the walls at an angle greater than the critical angle (above which total internal reflection no longer takes place). The invention can be utilized with a radius of curvature of the loop such that the angle of reflectance for some of the beam is greater than the critical angle, with a resultant drop in the throughput in the probe. It is noted, from the view of FIG. 2, that a greater number of reflections take place in the loop as compared to other portions of the optical waveguide element, such as the straight input section 37 and output section 40. Consequently, a much stronger interaction occurs at the loop 38 than would occur if a commensurate length of straight optical waveguide were exposed to the sample medium. Moreover, the curvature of the loop increases the angle of incidence of the beam during each reflection, which increases the number of reflections per unit length of waveguide element and potentially may affect the depth into the fluid with which the beam interacts. The relatively sharp tip provided by the loop 38 allows a relatively localized area of sample to be measured. For example, only the loop need be in contact with the sample, so that the probe tip may be placed into contact with a selected localized area of a solid but yieldable sample to determine the chemical composition of that localized area. If desired, the optical probe may be optimized for measurements on particular materials by selecting the radius of the loop 38.

In the probe of FIG. 2 a retaining structure 42, such as a metal clip, epoxy glue, or the like, is used to hold the input section 37 and the output section 40 adjacent one another as they extend away from the loop in the same direction and to maintain the loop 38 in its desired position. The tube 25 may serve as the retaining structure 42, in which case the waveguide sections 37 and 40 may extend back through the tube. However, the probe of the present invention may be formed as a unitary optical waveguide element having the loop 38 formed in it, such as by the retainer 42, to allow analysis of the sample medium in contact with the loop 38, with little or no interaction occurring in the input section 37 and output section 40, which preferably are not in contact with the sample (e.g., are exposed to air) or are shielded as with a coating.

Figure 3:
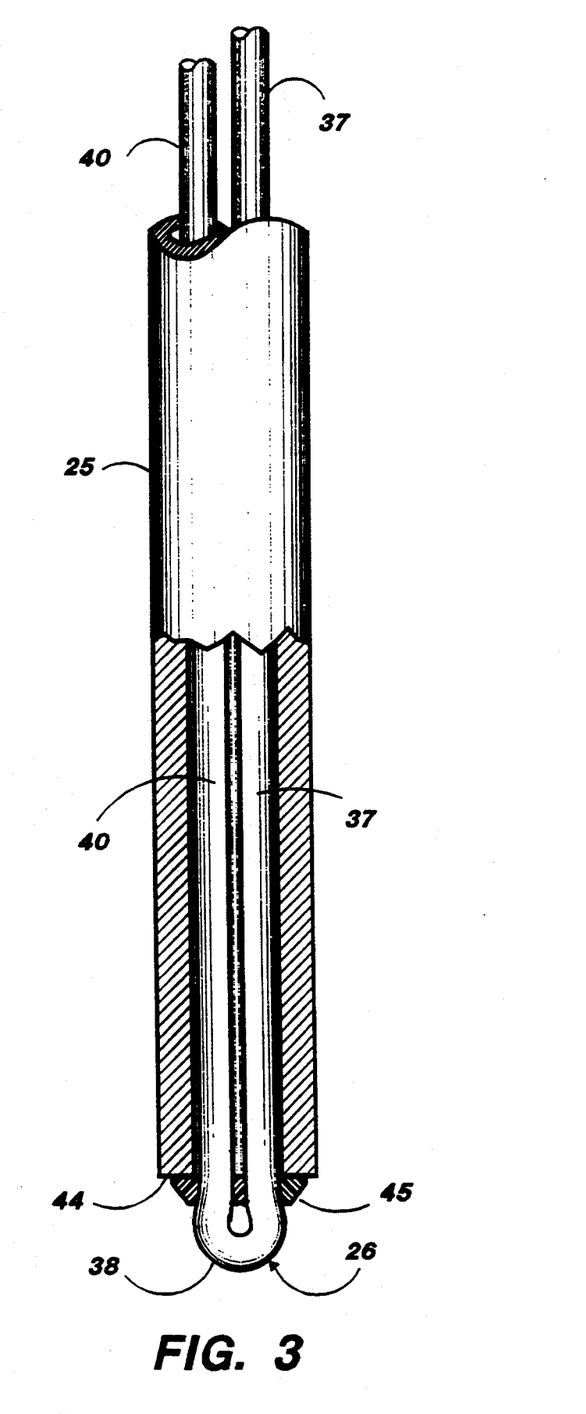
FIG. 3 is a view, partially in cross-section, of a portion of an optical probe in accordance with the present invention.

The probe 10 is shown in FIG. 3 with a portion of the tube 25 cut away to illustrate the input section 37 and output section 40 of the optical waveguide element held within the bore of the tube 25. The tube 25 may be made relatively thin, e.g., 3 mm in diameter, with an internal bore of 2 mm or less, and with optical waveguide elements in the range of 1 mm or less (e.g., 0.7 mm) diameter being held therein. The radius of curvature R of the loop is generally greater than the diameter of the waveguide, and with a waveguide diameter of 1 mm or less would typically be less than 2 mm. The tip 26 protrudes from the free end 44 of the tube 25 and forms the loop 38. Epoxy or other solid material 45 can be used to seal the bore of the tube 25 at its end 44, and to hold the optical waveguide element including the tip 38 in place on the tube. Moreover, the solid epoxy 45 also provides mechanical reinforcement to the loop 38 to support it against mechanical strains when the loop 38 is pressed against solid objects.

Figure 4:
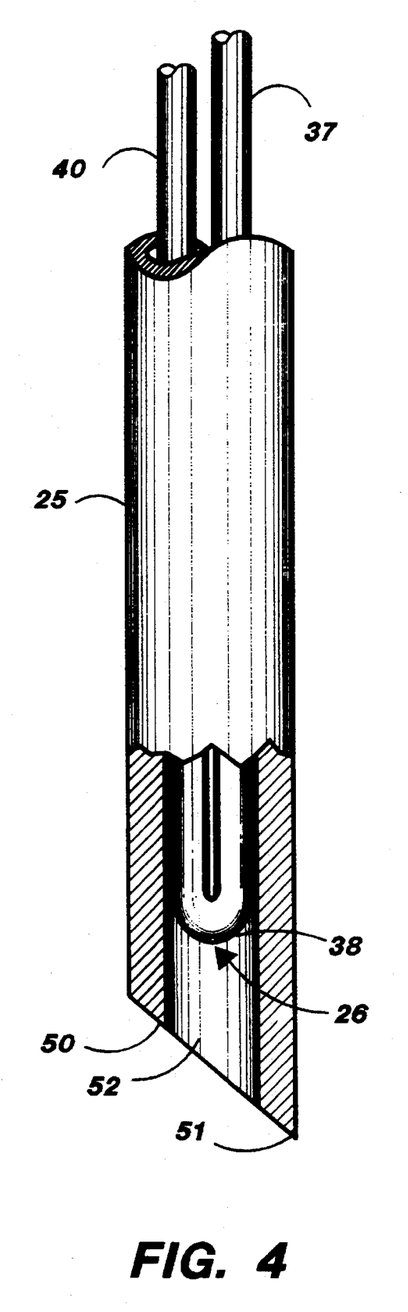
FIG. 4 is a view, partially in cross-section, of a portion of an optical probe in accordance with the present invention adapted to be injected under the skin of a subject for in vivo measurements.

Another embodiment of the probe 10 is shown in FIG. 4, wherein the tube 25 may be a cannula having a sharpened free end 50 which is cut off at an angle to form a sharpened point 51 adapted to penetrate solid materials, and which may be used as an injection needle for injecting under the skin or into blood vessels of a subject. The loop 38 may be withdrawn from the open end 50 of the tube 25, as shown in FIG. 4, during insertion of the tube into a subject, and then the optical waveguide sections 37 and 40 may be pushed forward through the bore 52 of the tube 25 to cause the loop 38 to extend outwardly from the end 50 of the tube. In this manner, the probe may be inserted into the blood stream of a subject in a manner analogous to the insertion of a catheter in the blood stream. However, the loop 38 may also be mounted and sealed adjacent to the open end 50 in a manner similar to that shown in FIG. 3 so that the loop 38 is always exposed but the sharpened tip 51 allows the cannula to be readily inserted under the skin.

Figure 5:
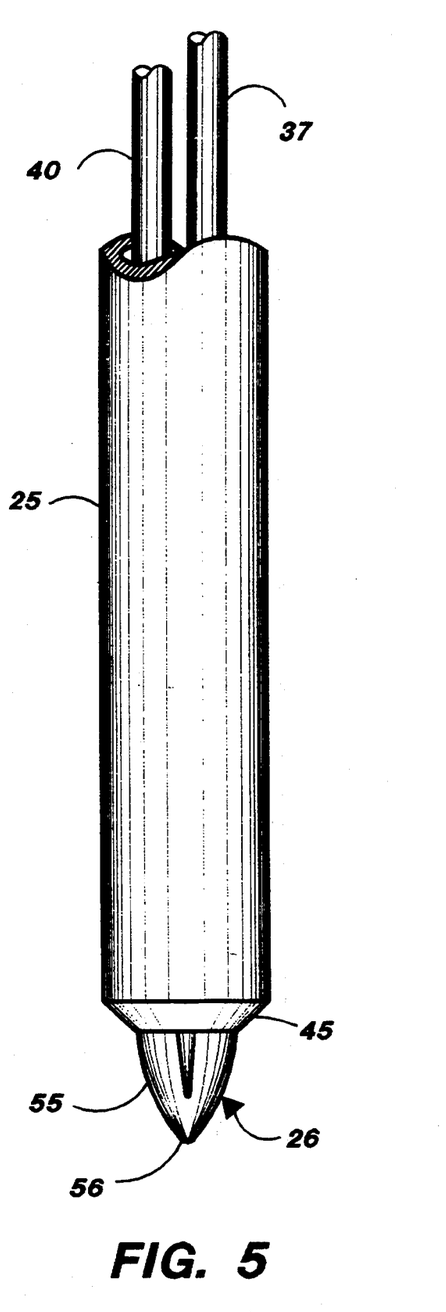
FIG. 5 is a view of a portion of an optical probe in accordance with the present invention having a sharpened tip which may be pressed into contact with soft material or injected under the skin of a subject.

An alternative structure that may be utilized to penetrate under the skin of subjects or into soft solid materials is shown in FIG. 5. The structure of the probe of FIG. 5 is similar to that of FIG. 3, but with the tip 26 being formed of a sharpened loop 55 which is shaped to taper to a relatively sharp point 56. This sharpened loop 55 may be formed, for example, by heating a portion of the optical waveguide element until it reaches a temperature at which the material of the element is somewhat plastic, and then bending and shaping the loop 55 in a form so that it acquires the relatively sharp point 56 illustrated in FIG. 5. The loop 55 may be secured to the tube 25 and the bore of the tube sealed off by epoxy or other sealant 45 in the same manner as illustrated in FIG. 3.

Figure 6:
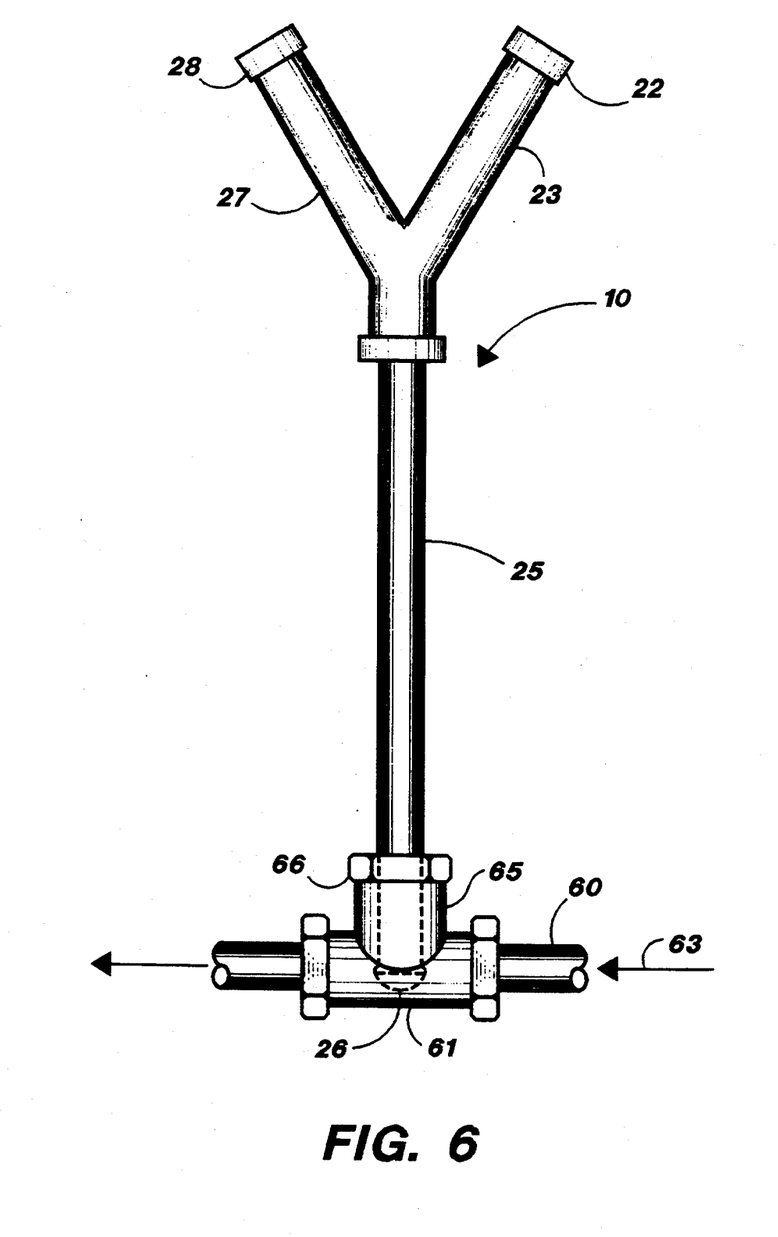
FIG. 6 is an exemplary view of an optical probe in accordance with the present invention mounted in a coupling for monitoring fluid flowing in a pipeline.

Another exemplary utilization of the probe 10 of the present invention is in measurement of flowing fluids, utilizing standard fittings. Such a use is illustrated in FIG. 6 in which a pipeline 60 having a tap coupling 61 connected therein has a fluid 63 flowing through it. The fluid 63 may be liquid or gas which is to be monitored utilizing the spectrometer of the invention. The tube 25, which can have a relatively small standard bore diameter, e.g., 3 mm, is inserted into the base 65 of the Tee fitting 61 and is secured in place by a standard press fit coupling 66, e.g., a SwageLok TM tube fitting. The operator can insert the tube 25 into the fitting 61 until the tip 26 is in the flow path of the fluid 63, and then tighten down the coupler 66 to provide a fluid tight coupling. The couplings 22 and 28 can be connected to fiber optic cables in the manner shown in FIG. 1 to allow operative connection to a spectrometer. In this manner, the flow of fluid in the relatively small pipeline 60 can be monitored by the spectrometer without having to draw a sample of fluid from the pipeline. The small size of the probe is also an advantage in larger pipes or reactors because it minimizes interferences and the dangers of putting a large sampling port in the side of a pipeline.

Figure 7:
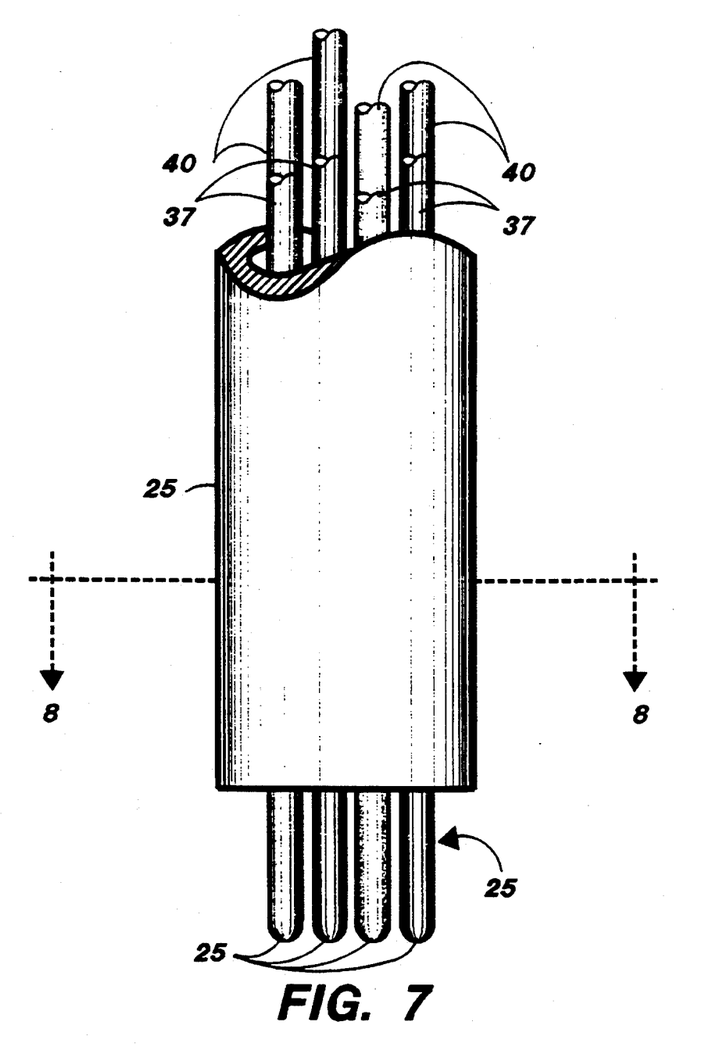
FIG. 7 is a view of a portion of another optical probe in accordance with the invention having multiple optical waveguide elements.
Figure 8:
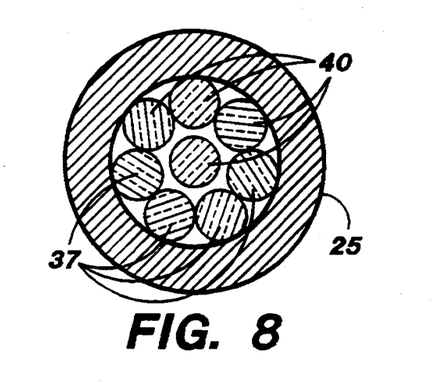
FIG. 8 is a cross-sectional view taken generally along the line 8—8 of FIG. 7 showing an optical element bundle which may be utilized as the optical waveguide element in the present invention.

As illustrated in FIG. 7, the probe of the present invention may utilize several optical waveguide elements bundled together to provide a tip 26 extending from the end of the probe tube 25 which has a plurality of loops 70. Each of the loops 70 may be formed in the same manner as the loop 38 of FIG. 3, or in other manners, for example, in the shape of the loop 55 of FIG. 5. By having multiple loops with multiple input and output sections, the relative throughput and signal strength of the spectroscopy system can be increased. As illustrated in the cross-sectional view of FIG. 8, a bundle of input waveguide sections 37 and output waveguide sections 40 can be extended through the bore of the tube 25. Although the loops 70 have been shown aligned in FIG. 7, it is also understood that they may be arranged in other manners, and a bundle of waveguide elements may be formed in a loop, if desired, to provide the tip 26.

A preferred material for the optical waveguide elements constituting the input section 37, the output section 40 and the loop 38 is chalcogenide glass where infrared spectroscopy is being carried out. Chalcogenide glass waveguides are typically transmissive to infrared in the spectral range of 7000 to 700 wave numbers. In addition, chalcogenide glass has a high refractive index providing good ATR performance, a low glass transition temperature, and good chemical resistance. Such glasses are available from several sources, exemplary sources being Isorad, Ltd., Israel, and Amorphorus Materials, Inc., Texas, U.S.A. A preferred glass composition is from the arsenic-selenium-tellurium system having a glass transition temperature sufficiently low to allow the loop to be readily formed. The loop can be formed in such material in various manners. One preferred manner is to heat a portion of an optical waveguide formed of such material having the desired diameter until the temperature of the heated portion is such that the material is somewhat plastic. The temperature to which the material is heated can be selected for the particular material and the diameter of the waveguide to yield satisfactory forming of the loop. The optical waveguide is then drawn over tooling such as a cold forming wire (or other tooling) having a radius of curvature substantially equal to the desired inside radius of the loop. The optical waveguide is drawn down over the forming wire until it cools and retains the radius of curvature imposed on it by the wire. The two portions of the optical waveguide that extend away from the loop may then be inserted in the bore of the hollow probe tube and pulled through the tube until the loop is adjacent the open end of the probe tube. As noted above, the end of the probe tube can be sealed, and the loop reinforced, by utilizing epoxy which may be placed around the end of the loop to seal off the bore of the tube when the epoxy is in a liquid state, with the epoxy then being cured and hardened. The probe tube itself may be formed of various materials, preferably a thin walled metal, such as stainless steel or aluminum. The optical waveguide forming the loop and input and output sections does not need to be flexible, and can be formed of rigid waveguide which can be cylindrical but need not be. In some circumstances, a rectangular cross-section, for example, may be used. Any suitable optical waveguide material may be used, depending on the wavelengths of the analytical radiation. As noted above, chalcogenide glass is preferred for infrared transmission and because it can be readily formed by heating.

It is understood that the invention is not confined to the particular embodiments described herein as illustrative, but embraces all such modified forms thereof as come within the scope of the following claims.

What is claimed is:

1. A probe for use in obtaining attenuated total reflectance measurements comprising:
   an optical waveguide element having a diameter of 1 mm or less and an input section, an output section and a loop therein which can be contacted with a sample to obtain attentuated total reflectance measurements, the optical waveguide element formed of an optical material which will transmit electromagnetic radiation of desired wavelengths, the loop being formed to retain a radius of curvature of the loop which is selected relative to the diameter of the waveguide element such that electromagnetic radiation in the optical waveguide element will execute substantially more reflections off the surfaces of the waveguide element in the loop than in the input and output sections adjacent to the loop such that attenuated total reflectance measurements can be obtained when the loop is in contact with a sample material on which the measurements are to be made, and a hollow tube engaging the input and output sections adjacent to the loop to hold them adjacent to one another and extending away from the loop in the same direction, the input and output sections of the optical waveguide element adjacent to the loop passing through a bore of the tube, with the loop extending from a free end of the tube.

2. The probe of claim 1 wherein the loop and the input and output sections of the optical waveguide element adjacent to the loop are free to move in the bore of the tube so that the loop can be withdrawn from the free end of the tube into the bore of the tube.

3. The probe of claim 2 wherein the retaining structure further includes material sealing the loop to the free end of the tube.

4. The probe of claim 1 further including a coupler on an end of each of the input and output sections of the optical waveguide element extending from the loop, the couplers suited for coupling electromagnetic radiation into and out of the optical waveguide element to an optical system.

5. The probe of claim 1 wherein the optical waveguide element is formed of chalcogenide glass.

6. The probe of claim 1 wherein the probe further comprises at least two of said optical waveguide elements with the tube engaging each of the input and output sections adjacent to the loops formed in each of the optical waveguide elements.

7. The probe of claim 1 wherein the free end of the tube is cut at an angle to form a sharpened point adapted to penetrate solid objects.

8. A probe for use in obtaining attenuated total reflectance measurements comprising:
   an optical waveguide element having an input section, an output section, and a loop between the input and output sections, the optical waveguide element formed of an optical material which will transmit electromagnetic radiation of desired wavelengths, the loop in the optical waveguide element having its surface exposed to allow attenuated total reflectance measurements and the loop being formed to retain a radius of curvature less than 2 mm; and
   an elongated thin walled tube having a hollow bore through which the input and output sections of the optical waveguide element extend adjacent to one another and each section having an end thereof extending out of the tube, the loop extending from a free end of the tube where it may be exposed to the material to be tested.

9. The probe of claim 8 further including a sealing material sealing the free end of the tube adjacent to the loop and providing support for the loop.

10. The probe of claim 9 wherein the material sealing the loop to the free end of the tube is epoxy.

11. The probe of claim 8 further including a coupler on and end of each of the input and output sections of the optical waveguide element extending from the loop, the couplers suited for coupling electromagnetic radiation into and out of the optical waveguide element to an optical system.

12. The probe of claim 8 wherein the optical waveguide element is formed of chalcogenide glass.

13. The probe of claim 8 wherein the optical waveguide element has a diameter less than 1 mm.

14. The probe of claim 8 wherein the probe further comprises at least two of said optical waveguide elements with the loop formed in each of the optical waveguide elements extending from the free end of the tube.

15. The probe of claim 8 wherein the thin walled tube is formed of metal.

16. The probe of claim 8 wherein the free end of the tube is cut at an angle to form a sharpened point adapted to penetrate solid objects.

17. A spectroscopic system comprising:
   an infrared spectrometer providing an output beam of infrared radiation and adapted to receive and detect a beam of infrared which has interacted with a sample to affect the spectrum of the radiation in the beam;
   a probe for attenuated total reflectance measurements comprising an optical waveguide element having an input section, an output section, and a loop between the input and output sections which can be contacted with a sample to obtain attentuated total reflectance measurements, the optical waveguide element formed of an optical material which will transmit infrared radiation of desired wavelengths, the loop being formed to retain a radius of curvature of the loop which is selected relative to the diameter of the optical waveguide element such that infrared radiation in the optical waveguide element will execute substantially more reflections off the surfaces of the waveguide element in the loop than in the input and output sections of the waveguide element adjacent to the loop such that attenuated total reflectance measurements can be obtained when the loop is in contact with the sample on which the measurements are to be made, and a hollow tube engaging the input and output sections adjacent to the loop to hold them adjacent to one another and extending away from the loop in the same direction, the input and output sections of the optical waveguide element passing through the bore of the tube, with the loop extending from a free end of the tube;
   optical coupling cables connected to the spectrometer and the probe to receive the output beam from the spectrometer and direct the beam from the spectrometer to the input section of the optical waveguide element of the probe, and to direct the infrared radiation from the output section of the probe back to the spectrometer.

18. The spectroscopic system of claim 17 wherein the loop and the input and output sections of the optical waveguide element adjacent to the loop are free to move in the bore of the tube so that the loop can be withdrawn from the free end of the tube into the bore of the tube.

19. The spectroscopic system of claim 17 wherein the hollow tube further includes material sealing the loop to the free end of the tube.

20. The spectroscopic system of claim 17 wherein the optical waveguide element of the probe is formed of chalcogenide glass.

21. The spectroscopic system of claim 17 wherein the optical waveguide element has a diameter less than 1 mm, and the radius of curvature of the loop is greater than the diameter of the optical waveguide element and less than 2 mm.

22. The spectroscopic system of claim 17 wherein the probe further comprises at least two of said optical waveguide elements with the tube engaging the input and output sections of each optical waveguide element to support the loop formed in each of the optical waveguide elements.

23. A method of carrying out attenuated total reflectance measurements on a sample, comprising the steps of:
   (a) providing an optical waveguide element having an input section, an output section, and a loop between the input and output sections, the loop having a radius of curvature of less than 2 mm and its surface exposed to allow attenuated total reflectance measurements, the optical waveguide element suited for transmitting desired wavelengths of electromagnetic radiation;
   (b) providing electromagnetic radiation to the input section of the optical waveguide element having a desired band of wavelengths of electromagnetic radiation and directing the electromagnetic radiation with the optical waveguide element through the loop and returning the electromagnetic radiation passed through the output section of the optical fiber to a spectrometer;
   (c) contacting the loop of the optical waveguide element with a localized portion of the sample while passing electromagnetic radiation therethrough to affect the electromagnetic radiation by attenuated total reflectance interaction between the electromagnetic radiation and the sample to obtain measurements by the spectrometer only on the localized portion of the sample contacted by the loop.

24. The method of claim 23 including retaining the input and output sections of the optical waveguide element in the bore of a thin walled tube with the loop formed as a tip extending from one end of the tube.

25. A probe for use in obtaining attenuated total reflectance measurements comprising:

an optical waveguide element having an input section, an output section and a loop therein which can be contacted with a sample to obtain attenuated total reflectance measurements, the optical waveguide element formed of an optical material which will transmit electromagnetic radiation of desired wavelengths, the optical waveguide element in the loop being shaped to taper to a point such that electromagnetic radiation in the optical waveguide element will execute substantially more reflections off the surfaces of the waveguide element in the loop than in the input and output sections adjacent to the loop such that attenuated total reflectance measurements can be obtained when the point of the loop is in contact with a sample material on which the measurements are to be made, and retaining structure engaging the input and output sections adjacent to the loop to hold them adjacent to one another and extending away from the loop in the same direction.

26. The probe of claim 25 wherein the retaining structure comprises a hollow tube, the input and output sections of the optical waveguide adjacent to the loop passing through a bore of the tube, with the loop extending from one end of the tube.

27. The probe of claim 26 wherein the hollow tube further includes material sealing the loop to the one end of the tube.

28. The probe of claim 25 wherein the optical waveguide element is formed of chalcogenide glass.

29. The probe of claim 25 wherein the optical waveguide element has a diameter less than 1 mm.

* * * * *